United States Patent
Dupin et al.

(10) Patent No.: US 10,842,776 B2
(45) Date of Patent: Nov. 24, 2020

(54) HYCANTHONE DERIVATIVES AND PRIMAQUINE DERIVATIVES FOR USE IN THE PREVENTION AND/OR THE TREATMENT OF DISORDERS ASSOCIATED TO GAMMAHERPESVIRUS

(71) Applicants: Assistance Publique—Hopitaux de Paris, Paris (FR); Institut National de la Sante et de la Recherche Medicale (INSERM), Paris (FR); Sorbonne Universite, Paris (FR); Universite Paris Descartes, Paris (FR); Centre National de la Recherche Scientifique (CNRS), Paris (FR)

(72) Inventors: Nicolas Dupin, Paris (FR); Anne-Geneviève Marcelin, Paris (FR); Vincent Calvez, Paris (FR); Philippe Grange, Ozoir la Ferrière (FR)

(73) Assignees: Assistance Publique—Hopitaua de Paris, Paris (FR); Institut National de la Sante et de la Recherche Medicale (INSERM), Paris (FR); Sorbonne Unicersite, Paris (FR); Universite Paris Descartes, Paris (FR); Centre National de la Recherche Scientifique (CNRS), Paris (FR)

( * ) Notice: Subject to any disclaimer, the term of this patent is extended or adjusted under 35 U.S.C. 154(b) by 11 days.

(21) Appl. No.: 16/312,459

(22) PCT Filed: Jun. 28, 2017

(86) PCT No.: PCT/EP2017/066020
§ 371 (c)(1),
(2) Date: Dec. 21, 2018

(87) PCT Pub. No.: WO2018/002153
PCT Pub. Date: Jan. 4, 2018

(65) Prior Publication Data
US 2019/0125723 A1    May 2, 2019

(30) Foreign Application Priority Data
Jun. 28, 2016    (EP) .................................... 16305782

(51) Int. Cl.
A61K 31/382    (2006.01)
A61K 45/06     (2006.01)
A61K 31/4706   (2006.01)
A61K 31/352    (2006.01)
A61P 31/22     (2006.01)

(52) U.S. Cl.
CPC .......... *A61K 31/382* (2013.01); *A61K 31/352* (2013.01); *A61K 31/4706* (2013.01); *A61K 45/06* (2013.01); *A61P 31/22* (2018.01)

(58) Field of Classification Search
None
See application file for complete search history.

(56) References Cited

U.S. PATENT DOCUMENTS

| 2,604,474 | A | 7/1952 | Elderfield et al. |
| 3,294,803 | A | 12/1966 | Rosi et al. |
| 3,312,598 | A | 4/1967 | Rosi et al. |

(Continued)

FOREIGN PATENT DOCUMENTS

| NL | 6410359 | 9/1964 |
| WO | WO 01/13907 | 3/2001 |

(Continued)

OTHER PUBLICATIONS

Erlendsson, CAS SciFinder English abstract of Ugeskrift for Laeger (1958), 120(25), pp. 804-809 (database Medline 1959010606).*

(Continued)

*Primary Examiner* — Brian J Davis
(74) *Attorney, Agent, or Firm* — Panitch Schwarze Belisario & Nadel LLP

(57) ABSTRACT

The present invention relates to compounds of the following general formula (I) or (II) or a pharmaceutically acceptable salt and/or solvate thereof, for use in the prevention and/or the treatment of disorders associated to gammaherpesvirinae, in particular to the human herpesvirus 8 (HHV8) or the human herpes virus 4 (HHV4), and pharmaceutical compositions containing such compounds.

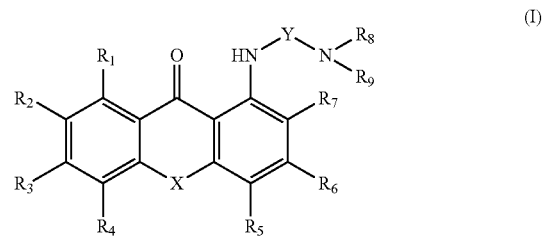

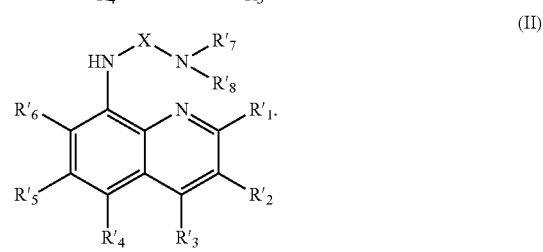

24 Claims, 5 Drawing Sheets

(56) References Cited

U.S. PATENT DOCUMENTS

2009/0317472 A1    12/2009   Kohn et al.
2011/0028564 A1    2/2011   Johansen et al.

FOREIGN PATENT DOCUMENTS

WO    WO 03/039546    5/2003
WO    WO 2016/011022 A1 *    1/2016   ........... A61K 31/382

OTHER PUBLICATIONS

Sulli et al., La Clinica Terapeutica (1963), vol. 27, pp. 132-168 (database Medline 1964058508).*
Erlendsson, Ugeskrift for Laeger (1958), 120(25), pp. 804-809.*
Sulli et al., La Clinica Terapeutica (1963), 27, pp. 132-168.*
Akin et al., Coinfection of Plasmodium vivax and Epstein-Barr virus: case report, 3(1) Asian Pacific Journal of Tropical Disease 74-75 (2013).
Carbone et al., EBV-Associated Lymphoproliferative Disorders: Classification and Treatment, 13 The Oncologist 577-585 (2008).
Cesarman, Gammaherpesviruses and Lymphoproliferative Disorders: Classification and Treatment, 9 Annual Rev. Pathol. Mech. 349-372 (2014).
Chêne et al., Effect of Acute Plasmodium falciparum Malaria on Reactivation and Shedding of the Eight Human Herpes Viruses, 6(10) PLoS One 1-7 (Oct. 2011).
Matsuno et al., Diethyldithiocarbamate induces apoptosis in HHV-8-infected primary effusion lymphoma cells via inhibition of the NF-κB pathway, 40 International Journal of Oncology 1071-1078 (2012).
Peltonen et al., Identification of Novel p53 Pathway Activating Small-Molecule Compounds Reveals Unexpected Similarities with Known Therapeutic Agents, 5(9) PLoS One 1-11 (Sep. 2010).
Uldrick et al., Update on KSHV-Epidemiology, Kaposi Sarcoma Pathogenesis, and Treatment of Kaposi Sarcoma, 305(2) Cancer Lett. 150-162 (Jun. 28, 2012).

* cited by examiner

HYCANTHONE DERIVATIVES AND PRIMAQUINE DERIVATIVES FOR USE IN THE PREVENTION AND/OR THE TREATMENT OF DISORDERS ASSOCIATED TO GAMMAHERPESVIRUS

CROSS-REFERENCE TO RELATED APPLICATIONS

This application is a U.S. National Stage Application pursuant to 35 U.S.C. § 371 of International Patent Application PCT/EP2017/066020, filed on Jun. 28, 2017, and published as WO 2018/002153 on Jan. 4, 2018, which claims priority to European Patent Application 16305782.1, filed on Jun. 28, 2016, all of which are incorporated herein by reference in their entireties for all purposes.

TECHNICAL FIELD

The present invention relates to two families of compounds, Primaquine derivatives and Hycanthone derivatives for use in the prevention and/or the treatment of disorders associated to gammaherpesvirinae such as the human herpesvirus 8 (HHV8), also called Kaposi's sarcoma herpes virus (KSHV), and the human herpes virus 4 (HHV4), also called Epstein-Barr virus (EBV). The present invention also relates to a pharmaceutical composition comprising said compounds for use in the prevention and/or the treatment of disorders associated to gammaherpesvirinae.

BACKGROUND INFORMATION

The burden of viral infections in cancer is high but underappreciated by much of the cancer research community. The International Agency for Research on Cancer estimates that one in five cancer cases worldwide are caused by infection, with most caused by viruses. These cancers are particular public health problems for the developing world, as well as for underserved and immunosuppressed populations in developed countries. Most importantly, these cancers have readily identifiable targets for diagnosis, prevention and therapy.

Infectious cancer agents (including, viruses, bacteria and parasites) have been divided into two broad categories: direct carcinogens, which express viral oncogenes that directly contribute to cancer cell transformation, and indirect carcinogens that presumably cause cancer through chronic infection and inflammation, which eventually leads to carcinogenic mutations in host cells. By definition, a direct viral carcinogen is present in each cancer cell and expresses at least one transcript to maintain the transformed tumor cell phenotype, as occurs with HPV-, MCV-, EBV- and KSHV-related cancers. Evidence supporting this comes from knockdown studies in which the loss of viral proteins results in the loss of host cancer viability. Studies on the large DNA tumor viruses (such as EBV and KSHV) suggest a complex interaction between the viral oncogenes and the host cell that may have more to do with evading immune responses during latency than ensuring viral genome replication. During lytic viral replication, these viruses also hijack the cell cycle regulation machinery to promote their own genomic replication. The oncogenic herpesviruses encode proteins to inhibit RB1 and other tumor suppressor checkpoints during active lytic viral replication, and also possess virally encoded DNA synthesis enzymes. These viral genes, like their counterparts among the small DNA tumor viruses, set the stage for the rapid replication and amplification of viral genomes by generating an S phase-like cellular state that can replicate viral DNA once lytic replication is initiated.

But the viral proteins and virus-encoded miRNAs that drive herpesviral tumors are expressed during latency, and these viral oncogenes cannot directly contribute to productive viral replication. Herpesvirus oncoproteins are expressed at the wrong time for them to be involved in generating the cellular resources needed for virus genome replication. The KSHV LANAI oncoprotein suppresses lytic replication to maintain virus latency while it simultaneously targets RB1 and interferon signaling responses. The KSHV-encoded cyclin is another latent viral oncoprotein that is expressed in a cell cycle-dependent manner. Similar to HPV E7, it targets RB1 and inactivates the G1/S checkpoint but it does not promote virus replication.

It is now 20 years since the discovery by Yuan Chang, Patrick Moore, and their colleagues of DNA from a novel herpesvirus in biopsy specimens of human Kaposi sarcoma (KS). That virus, now called KS-associated herpesvirus (KSHV) or human herpesvirus 8 (HHV-8), has since been cloned and sequenced, grown in culture, and extensively studied in vitro. Epidemiologic studies provide strong evidence that infection by KSHV is required for KS tumorigenesis and further link the viral genome to at least two lymphoproliferative disorders: primary effusion lymphoma (PEL) and multicentric Castleman disease (MCD).

The best-characterized latent genes constitute a major latency locus that is transcribed in all latently infected cells. This region includes several ORFs, encoding the proteins latency-associated nuclear antigen (LANA), viral cyclin (v-cyclin), v-Flice-inhibitory protein (v-FLIP), and kaposins A, B, and C. The first three genes are under the control of a single promoter (the LANA promoter, or LTc), which generates a series of coterminal mRNAs via differential splicing. A second promoter (the kaposin promoter, or LTd) encodes a spliced transcript encoding the kaposins and can also generate a bicistronic RNA for v-cyclin and v-FLIP. This promoter also governs the expression of 12 pre-miRNAs, which can be processed to yield a total of 18 mature miRNAs. All of these latent products have been found to be expressed in KS spindle cells as well as PEL cells.

There are many factors that allow KSHV to block apoptosis in KSVH infected cells:

KSHV v-FLIP is a potent antiapoptotic effector: for example, siRNA-mediated inactivation of v-FLIP provokes apoptosis in PEL cells. v-FLIP's prosurvival activity is linked to its ability to activate the transcription factor NF-κB. NF-κB is maintained in cells in an inactive cytoplasmic form, bound to the inhibitor IκB. v-FLIP binds and activates the γ subunit of IκB kinase (IKK). The resulting IκB phosphorylation displaces IκB from NF-κB, releasing the active transcription factor to the nucleus, where it activates a large panel of antiapoptotic and proinflammatory genes. Expression of v-FLIP in spindle cells thus not only can extend their lifespan but also can explain, at least in part, the inflammatory phenotype of KS lesions. NF-κB activation by v-FLIP expression in endothelial cells has also been linked to a third phenotype relevant to KS—the dramatic rearrangement of the cytoskeleton that gives the cells their characteristic spindle shape.

KSHV encode for 12 miRNAs which are clustered in the vicinity of the major latency transcript: 3 of them (miR-K12-1, K12-3 & K12-4-3p) contribute to the inhibition of apoptosis targeting the apoptosis effector caspase 3.

The Epstein-Barr virus (EBV), also called human herpesvirus 4 (HHV-4), is a latent Gamma-herpesvirus that infects more than 90% of the world's population. Primary lytic infection occurs in the oropharynx and may be asymptomatic or present as infectious mononucleosis. EBV is highly immunogenic; and during primary infection, normal persons mount a vigorous humoral and cellular immune response with the cellular component consisting of CD4 and CD8 T cells, which control both primary infection and the periodic reactivations that occur in all EBV-seropositive persons. Indeed, analyses using multimers to enumerate EBV-specific T cells have shown that up to 1% to 5% of circulating T cells in a normal EBV-seropositive person may be specific for EBV. After clearance of primary infection, EBV persists as an episome in infected B cells, establishing latent infection characterized by the expression of only a limited array of subdominant EBV antigens.

This virus has been associated with infectious mononucleosis (glandular fever); some lymproliferative disorders such as Hodgkin's lymphoma, Burkitt's lymphoma, central nervous system lymphomas, plasmablastic lymphoma, diffuse large B cell lymphoma and primary effusion lymphoma; some non-lymphoid malignancies such as nasopharyngeal carcinoma and gastric cancer; and some autoimmune diseases such as Dermatomyositis, systemic lupus erythematosus, rheumatoid arthritis, Sjögren's syndrome, multiple sclerosis (*Annu. Rev. Pathol. Mech. Dis.* 2014. 9:349-72, *E Cesarman—The Oncologist* 2008; 13:577-585, A Carbone).

To date, a need exists for preventing and/or a treating disorders associated to gammaherpesvirinae, in particular the human herpesvirus 8 (HHV8) or the human herpes virus 4 (HHV4).

Previous studies have shown that when one of the factors blocking apoptosis (for example v-Flip using one siRNA) is inactivated, this induces a cell death of KSHV infected cells evidence and that apoptosis induction is one of the key strategy that can be developed searching for new treatment for Kaposi sarcoma and other gammaherpesvirinae associated diseases.

BRIEF SUMMARY OF THE INVENTION

The inventors of the present invention have thus discovered two families of compounds, Primaquine derivatives and Hycanthone derivatives for use in the prevention and/or the treatment of disorders associated to the human herpesvirus 8 (HHV8). These molecules induce HHV8 infected cell death by apoptosis while not inducing toxicity in primary cells not infected with HHV8.

Thus, a first object of the invention is a compound of the following general formula (I):

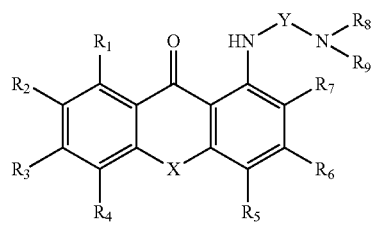

(I)

or a pharmaceutically acceptable salt and/or solvate thereof, wherein:
X is an oxygen or a sulfur atom;
Y is a $(C_1-C_{10})$alkyl group;

$R_1$ to $R_4$ are, independently of one another, hydrogen atom, halo, $—CF_3$, $—CN$, $—CO_2R_{10}$, $—COR_{11}$, $—CONR_{12}R_{13}$, $—NO_2$, or a group selected from $(C_1-C_6)$alkyl, $(C_2-C_6)$alkenyl and $(C_2-C_6)$alkynyl;

$R_5$ to $R_7$ are, independently of one another, hydrogen atom or a group selected from $(C_1-C_6)$alkyl, $—OR_{14}$, $—NR_{15}R_{16}$, $—CONR_{17}R_{18}$, $—CO(NR_{19}R_{20})_2$, $—SR_{21}$, $—COR_{22}$, $—COOR_{23}$, $—SO_2R_{24}$, $—NO_2$ and $—NO^+$, said $(C_1-C_6)$alkyl group being optionally substituted with one or several groups selected from halo, $—OR_{25}$, $—NR_{26}R_{27}$, $—CONR_{28}R_{29}$, $—CO(NR_{30}R_{31})_2$, $—SR_{32}$, $—COR_{33}$, $—COOR_{34}$, $—SO_2R_{35}$, $—NO_2$ and $—NO^+$;

$R_8$ and $R_9$ are, independently of one another, hydrogen atom or a $(C_1-C_{10})$alkyl group optionally substituted with OH, or $R_8$ and $R_9$ form together with the nitrogen atom to which they are chemically linked, an heterocycle;

$R_{10}$ to $R_{35}$ are, independently of one another, hydrogen atom, halo or a $(C_1-C_6)$alkyl group;

for use in the prevention and/or the treatment of disorders associated to gammaherpesvirinae, in particular to the human herpesvirus 8 (HHV8) or the human herpes virus 4 (HHV4).

A second object of the invention is a compound of the following general formula (II):

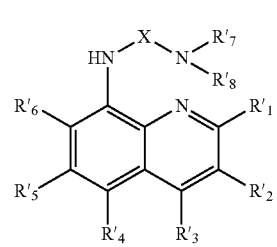

(II)

or a pharmaceutically acceptable salt and/or solvate thereof, wherein:
X is a $(C_1-C_{10})$alkyl group;
$R'_1$ to $R'_3$ are, independently of one another, hydrogen atom, halo, $—OR'_9$, $—R'_{10}OR'_{11}$, $—SR'_{12}$, $—COSR'_{13}$, $—NR'_{14}R'_{15}$, $—COR'_{16}$, $—COOR'_{17}$ or a $(C_1-C_6)$alkyl group;
$R'_4$ to $R'_6$ are, independently of one another, hydrogen atom, halo, $—OR'_{18}$, $—R'_{19}OR'_{20}$, $—SR_{21}$ or $—NR_{22}R_{23}$;
$R'_7$ and $R'_8$ are, independently of one another, hydrogen atom or a $(C_1-C_{10})$alkyl group, or $R'_7$ and $R'_8$ form together with the nitrogen atom to which they are chemically linked, an heterocycle;
$R'_9$ to $R'_{23}$ are, independently of one another, hydrogen atom, halo or a group selected from $(C_1-C_6)$alkyl, aryl, $(C_1-C_6)$alkylaryl group for use in the prevention and/or the treatment of disorders associated to gammaherpesvirinae, in particular to the human herpesvirus 8 (HHV8) or the human herpes virus 4 (HHV4).

A third object of the present invention relates to a pharmaceutical composition comprising at least one compound of general formula (I) and/or one compound of general formula (II) and at least one pharmaceutically acceptable excipient, for use in the prevention and/or the treatment of disorders associated to gammaherpesvirinae, in particular to the human herpesvirus 8 (HHV8) or the human herpes virus 4 (HHV4).

Definition

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The terms "$(C_1-C_{10})$alkyl", as used in the present invention, refers to a straight or branched saturated hydrocarbon chain containing from 1 to 10 carbon atoms including, but not limited to, methyl, ethyl, n-propyl, iso-propyl, n-butyl, iso-butyl, sec-butyl, tert-butyl, n-pentyl, iso-pentyl, sec-pentyl, tert-pentyl, n-hexyl, iso-hexyl, sec-hexyl, tert-hexyl, n-heptyl, n-octyl, n-nonyl, n-decyl, and the like.

The terms "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, iso-pentyl, sec-pentyl, tert-pentyl, n-hexyl, iso-hexyl, sec-hexyl, tert-hexyl, and the like.

The term "$(C_2-C_6)$alkenyl", as used in the present invention, refers to a straight or branched unsaturated hydrocarbon chain containing from 2 to 6 carbon atoms and comprising at least one double bond, including, but not limited to, ethenyl, propenyl, butenyl, pentenyl, hexenyl and the like. It can be in particular an allyl group.

The term "$(C_2-C_6)$alkynyl", as used in the present invention, refers to a straight or branched unsaturated hydrocarbon chain containing from 2 to 6 carbon atoms and comprising at least one triple bond, including, but not limited to, ethynyl, propynyl, butynyl, pentynyl, hexynyl and the like.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group. Advantageously, it will be a phenyl group.

The term "$(C_1-C_6)$alkylaryl", as used in the present invention, refers to an aryl group as defined above bound to the molecule via a $(C_1-C_6)$alkyl group as defined above. In particular, the $(C_1-C_6)$alkylaryl group is a benzyl group.

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc. In particular, the heterocycle is piperidine or piperazine.

The term "nitrogen-containing heterocycle" as used in the present invention refers to a heterocycle as defined above containing at least one nitrogen atom.

Such a nitrogen-containing heterocycle is thus a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, at least one of the heteroatom(s) being a nitrogen atom, and notably all the heteroatoms are nitrogen. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members, in which one carbon atom has been replaced with a nitrogen atom and optionally 1 to 3, notably 1, additional carbon atom(s) has/have each been replaced with a nitrogen or oxygen atom, notably a nitrogen atom.

A nitrogen-containing heterocycle can be notably pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc. In particular, the heterocycle is piperidine or piperazine.

The term "halogen", as used in the present invention, refers to a fluorine, bromine, chlorine or iodine atom.

DETAILED DESCRIPTION OF THE INVENTION

Hycanthone derivatives According to a particular embodiment of the first object of the present invention, in the compound of the general formula (I) or a pharmaceutically acceptable salt and/or solvate thereof for use in the prevention and/or the treatment of disorders associated to the human herpesvirus 8 (HHV8), X is a sulfur atom.

In a preferred embodiment, in the compound of the general formula (I), Y is a $(C_1\text{-}C_6)$alkyl group, preferably Y is an ethyl.

In particular, the compound of the first object of the present invention is a compound of the following general formula (Ia):

(Ia)

In the compound of general formula (I) or (Ia), $R_8$ and $R_9$ particularly form together with the nitrogen atom to which they are chemically linked, an heterocycle, preferably a nitrogen-containing heterocycle, more preferably a piperidyl, pyrrolidyl or piperazyl, notably piperidyl.

In a preferred embodiment, in the compound of the general formula (I) or (Ia), $R_8$ and $R_9$ are, independently of one another, a $(C_1\text{-}C_{10})$alkyl group, preferably a $(C_1\text{-}C_6)$ alkyl group, more preferably an ethyl.

In a preferred embodiment, in the compound of the general formula (I) or (Ia), $R_1$ to $R_4$ are, independently of one another, hydrogen atom, halo, or a group selected from $(C_1\text{-}C_6)$alkyl and $(C_2\text{-}C_6)$alkenyl.

In particular, $R_1$ to $R_4$ are hydrogen atom.

In the compound of general formula (I) or (Ia), $R_5$ to $R_7$ are, independently of one another, hydrogen atom or a group selected from $(C_1\text{-}C_6)$alkyl, —$OR_{14}$, —$NR_{15}R_{16}$, —$CONR_{17}R_{18}$, —$CO(NR_{19}R_{20})_2$, —$SR_{21}$, —$COR_{22}$, —$COOR_{23}$, —$SO_2R_{24}$, —$NO_2$ and —$NO^+$, said $(C_1\text{-}C_6)$ alkyl group being optionally substituted with one or several groups selected from halo, —$OR_{25}$, —$NR_{26}R_{27}$, —$CONR_{28}R_{29}$, —$CO(NR_{30}R_{31})_2$, —$SR_{32}$, —$COR_{33}$, —$COOR_{34}$, —$SO_2R_{35}$, —$NO_2$ and —$NO^+$. $R_{14}$ to $R_{35}$ being as defined above.

In particular, $R_5$ to $R_7$ are, independently of one another, hydrogen atom or a $(C_1\text{-}C_6)$alkyl group, said $(C_1\text{-}C_6)$alkyl group being optionally substituted with one or several groups selected from halo, —$OR_{25}$, —$NR_{26}R_{27}$, —$CONR_{28}R_{29}$, —$CO(NR_{30}R_{31})_2$, —$SR_{32}$, —$COR_{33}$, —$COOR_{34}$, —$SO_2R_{35}$, —$NO_2$ and —$NO^+$. $R_{25}$ to $R_{35}$ being as defined above.

$R_5$ to $R_7$ represent particularly, independently of one another, hydrogen atom or a $(C_1\text{-}C_6)$alkyl group optionally substituted with one or several groups selected from, halo, —$OR_{25}$, —$NR_{26}R_{27}$, —$CONR_{28}R_{29}$, —$CO(NR_{30}R_{31})_2$ and —$SR_{32}$, preferably —$OR_{25}$, —$NR_{26}R_{27}$ and —$SR_{32}$, more preferably —$OR_{25}$. $R_{25}$ to $R_{32}$ being as defined above.

$R_5$ to $R_7$ represent in particular, independently of one another, hydrogen atom or a $(C_1\text{-}C_6)$alkyl group optionally substituted with one or several groups selected from, halo, —$OR_{25}$, —$NR_{26}R_{27}$, —$CONR_{28}R_{29}$, —$CO(NR_{30}R_{31})_2$ and —$SR_{32}$, preferably —$OR_{25}$, —$NR_{26}R_{27}$ and —$SR_{32}$, more preferably —$OR_{25}$. $R_{24}$ to $R_{32}$ being as defined above.

In particular, $R_6$ and $R_7$ are hydrogen atom and $R_5$ is hydrogen atom or a $(C_1\text{-}C_6)$alkyl group substituted with OH. More particularly, $R_6$ and $R_7$ are hydrogen atom and $R_5$ is a methyl substituted with OH.

In the above definitions of $R_5$ to $R_7$, the $(C_1\text{-}C_6)$alkyl is preferably methyl or ethyl, more preferably methyl.

In the above definitions of $R_5$ to $R_7$, $R_{14}$ to $R_{23}$ are, independently of one another, hydrogen atom, halo or a $(C_1\text{-}C_6)$alkyl group, preferably hydrogen atom or a $(C_1\text{-}C_6)$ alkyl group, more preferably hydrogen atom.

In a particular embodiment of the first object of the invention, in the compound of general formula (Ia):
- $R_8$ and $R_9$ are ethyl;
- $R_1$ to $R_4$ are hydrogen atom; and
- $R_5$ to $R_7$ are, independently of one another, hydrogen atom or a $(C_1\text{-}C_6)$alkyl group optionally substituted with one or several groups selected from —$OR_{25}$, —$NR_{26}R_{27}$ and —$SR_{32}$, more preferably —$OR_{25}$; $R_{25}$ to $R_{32}$ being as defined above.

In a particular embodiment of the first object of the invention, in the compound of general formula (Ia):
- $R_8$ and $R_9$ are ethyl;
- $R_1$ to $R_4$ are hydrogen atom;
- $R_6$ and $R_7$ are hydrogen atom; and
- $R_5$ is hydrogen atom or a $(C_1\text{-}C_6)$alkyl group optionally substituted with one or several groups selected from —$OR_{25}$, —$NR_{26}R_{27}$ and —$SR_{32}$, more preferably —$OR_{25}$; $R_{25}$ to $R_{32}$ being as defined above.

In a particular embodiment of the first object of the invention, in the compound of general formula (Ia):
- $R_8$ and $R_9$ are ethyl;
- $R_1$ to $R_4$ are hydrogen atom;
- $R_6$ and $R_7$ are hydrogen atom; and
- $R_5$ is hydrogen atom or a $(C_1\text{-}C_6)$alkyl group substituted with OH.

In a particular embodiment of the first object of the invention, the compound of general formula (I) can be a compound of the following formula (Ib), commonly named Hycanthone:

and the pharmaceutically acceptable salts and solvates thereof, in particular its mesylate salt including $CH_3SO_2O^-$.

According to one particular embodiment, the present invention is directed to the compound of general formula (I) as defined above for use in the prevention and/or the treatment of disorders associated to gammaherpesvirinae, in particular to the human herpesvirus 8 (HHV8) or the human herpes virus 4 (HHV4).

The present invention also relates to a method for preventing and/or for treating disorders associated to gammaherpesvirinae, in particular to the human herpesvirus 8 (HHV8) or the human herpes virus 4 (HHV4), comprising the administration to a person in need thereof of an effective dose of a compound of formula (I) as defined above.

The present invention also relates to the use of a compound of formula (I) as defined above, for the manufacture of a drug for the prevention and/or the treatment of disorders associated to gammaherpesvirinae, in particular to the human herpesvirus 8 (HHV8) or the human herpes virus 4 (HHV4).

The disorders associated to the human herpesvirus 8 (HHV8) may be in particular human Kaposi sarcoma (KS), primary effusion lymphoma (PEL) and multicentric Castleman disease (MCD).

The disorders associated to the human herpes virus 4 (HHV4) may be infectious mononucleosis (glandular fever) and some:

lymproliferative disorders such as Hodgkin's lymphoma, Burkitt's lymphoma, central nervous system lymphomas, plasmablastic lymphoma, diffuse large B cell lymphoma and primary effusion lymphoma;

non lymphoid malignancies such as nasopharyngeal carcinoma and gastric cancer;

autoimmune diseases such as Dermatomyositis, systemic lupus erythematosus, rheumatoid arthritis, Sjögren's syndrome, multiple sclerosis.

According to a particular embodiment, the compound of the first object of the invention is not a compound of general formula (I) in which:

X is a sulfur atom;

Y is ethyl;

$R_1$ to $R_4$, $R_6$ and $R_7$ are hydrogen atoms;

$R_5$ is methyl; and $R_8$ and $R_9$ are ethyl.

Primaquine Derivatives

According to a particular embodiment of the second object of the present invention, in the compound of the general formula (II) or a pharmaceutically acceptable salt and/or solvate thereof for use in the prevention and/or the treatment of disorders associated to the human herpesvirus 8 (HHV8), X is a $(C_1-C_6)$alkyl group.

In particular, X is n-butyl, iso-butyl, sec-butyl, tert-butyl, n-pentyl, iso-pentyl, sec-pentyl, tert-pentyl, n-hexyl, iso-hexyl, sec-hexyl or tert-hexyl. Preferably, X is sec-butyl, sec-pentyl or sec-hexyl. More preferably, X is sec-pentyl.

In particular, the compound of the first object of the present invention is a compound of the following general formula (IIa):

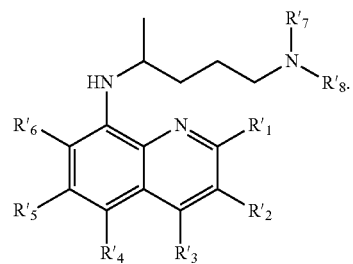

In the compound of general formula (II) or (IIa), $R'_7$ and $R'_8$ particularly form together with the nitrogen atom to which they are chemically linked, an heterocycle, preferably a nitrogen-containing heterocycle, more preferably a piperidyl, pyrrolidyl or piperazyl, notably piperidyl.

In a particular embodiment, in the compound of the general formula (II) or (IIa), $R'_7$ and $R'_8$ are, independently of one another, a $(C_1-C_{10})$alkyl group, more particularly a $(C_1-C_6)$alkyl group, notably an ethyl.

In a preferred embodiment, in the compound of the general formula (II) or (IIa), $R'_7$ and $R'_8$ are hydrogen atom.

In a preferred embodiment, in the compound of the general formula (II) or (IIa), $R'_1$ to $R'_3$ are, independently of one another, hydrogen atom, halo, —$OR'_9$, —$SR'_{12}$, —$COSR'_{13}$, —$NR'_{14}R'_{15}$ or a $(C_1-C_6)$alkyl group, preferably $R'_1$ to $R'_3$ are hydrogen atom.

In the above definition of $R'_1$ to $R'_3$, $R'_9$ and $R'_{12}$ to $R'_{15}$ are, independently of one another, hydrogen atom, halo or a group selected from $(C_1-C_6)$alkyl, aryl, $(C_1-C_6)$alkylaryl group. Preferably, $R'_9$ and $R'_{12}$ to $R'_{15}$ are, independently of one another, $(C_1-C_6)$alkyl, phenyl or benzyl.

In a preferred embodiment, in the compound of the general formula (II) or (IIa), $R'_4$ to $R'_6$ are, independently of one another, hydrogen atom, halo, —$OR'_{18}$ or —$R'_{19}OR'_{20}$.

In particular, $R'_4$ and $R'_6$ are hydrogen atom and $R'_5$ is —$OR'_{18}$;

In the above definition of $R'_4$ to $R'_6$, $R'_{18}$ to $R'_{20}$ are, independently of one another, hydrogen atom, halo or a group selected from $(C_1-C_6)$alkyl, aryl or $(C_1-C_6)$alkylaryl group, preferably $R'_{15}$ to $R'_{20}$ are, independently of one another, an hydrogen atom or a $(C_1-C_6)$alkyl group, more preferably $R'_{15}$ to $R'_{20}$ are, independently of one another, hydrogen atom or methyl.

In a particular embodiment of the second object of the invention, in the compound of general formula (II):

$R'_1$ to $R'_3$, $R'_7$ and $R'_8$ are hydrogen atom; and $R'_4$ to $R'_6$ are, independently of one another, hydrogen atom, halo, —$OR'_{18}$ or —$R'_{19}OR'_{20}$; $R'_{15}$ to $R'_{20}$ being as defined above.

In a particular embodiment of the second object of the invention, in the compound of general formula (II):

$R'_1$ to $R'_3$, $R'_7$ and $R'_8$ are hydrogen atom;

$R'_4$ and $R'_6$ are hydrogen atom; and $R'_5$ is —$OR'_{18}$; $R'_{18}$ being as defined above.

In a particular embodiment of the second object of the invention, the compound of general formula (II) or (IIa) is in the form of a salt of phosphinic acid.

In a particular embodiment of the second object of the invention, the compound of general formula (II) can be a compound of the following formula (IIb), commonly named Primaquine:

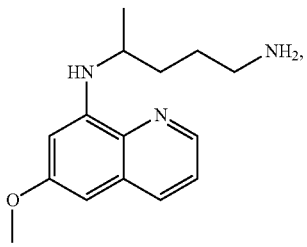

and the pharmaceutically acceptable salts and solvates thereof, in particular its phosphate salt.

Preferably the compound of general formula (II) can be diphosphate Primaquine.

According to one particular embodiment, the present invention is directed to the compound of general formula (II) as defined above for use in the prevention and/or the treatment of disorders associated to the gammaherpesvirinae, in particular to human herpesvirus 8 (HHV8) or the human herpes virus 4 (HHV4).

The present invention also relates to a method for preventing and/or for treating disorders associated to gammaherpesvirinae, in particular to the human herpesvirus 8 (HHV8) or the human herpes virus 4 (HHV4), comprising the administration to a person in need thereof of an effective dose of a compound of formula (II) as defined above.

The present invention also relates to the use of a compound of formula (II) as defined above, for the manufacture of a drug for the prevention and/or the treatment of disorders associated to gammaherpesvirinae, in particular to the human herpesvirus 8 (HHV8) or the human herpes virus 4 (HHV4).

The disorders associated to the human herpesvirus 8 (HHV8) may be in particular human Kaposi sarcoma (KS), primary effusion lymphoma (PEL) and multicentric Castleman disease (MCD).

The disorders associated to the human herpes virus 4 (HHV4) may be infectious mononucleosis (glandular fever) and some:
  lymproliferative disorders such as Hodgkin's lymphoma, Burkitt's lymphoma, central nervous system lymphomas, plasmablastic lymphoma, diffuse large B cell lymphoma and primary effusion lymphoma;
  non lymphoid malignancies such as nasopharyngeal carcinoma and gastric cancer;
  autoimmune diseases such as Dermatomyositis, systemic lupus erythematosus, rheumatoid arthritis, Sjögren's syndrome, multiple sclerosis;

Pharmaceutical Composition

The present invention also relates to a pharmaceutical composition comprising at least one compound of formula (I) or of formula (II) as defined above and at least one pharmaceutically acceptable excipient, for use in the prevention and/or the treatment of disorders associated to the human herpesvirus 8 (HHV8).

The pharmaceutical compositions according to the invention may be formulated notably for topical administration, oral administration or for injection, wherein said compositions are intended for mammals, including humans. The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The pharmaceutical compositions according to the invention may also be administered topically by all the means and in particular cream, gel, stick or serum The active ingredient may be administered in unit dosage forms of administration, in mixture with standard pharmaceutical carriers, to animals or to humans.

The pharmaceutical compositions according to the invention may further comprise at least one other active ingredient, used for treatment of HHV8 and or EBV associated diseases, such as Bleomycine (Bléomycine®), Vinblastine (Velbé®), paclitaxel and docetaxel, daunorubicine liposomiale (daunoXone), adriamycine, vincristine, navelbine, gemcitabine, interferon α (Roféron-A®, IntronA®), all-transretinoic acid (Atra®), thalidomide, IL-12, IL-4, Panretin, Revlimid, lenalinomide, rituximab, etoposide, cyclophosphamide, doxorubicin, vincristin, prednisone (CHOP), cidofovir, foscarnet, ganciclovir, valganciclovir, Tocilizumab, siltuximab, bortezomib, RNAi against LANA and/or vFlip, Hydroxyurea, Rapamycin.

The present invention relates also to a pharmaceutical composition comprising:
  (i) at least one compound of formula (I) or of formula (II) as defined above, and
  (ii) at least one other active ingredient, such as a chemotherapeutic agent, as a combination product for simultaneous, separate or sequential use.

According to one particular embodiment, the present invention is directed to the pharmaceutical composition as defined above for use in the prevention and/or the treatment of disorders associated to the human herpesvirus 8 (HHV8).

The present invention also relates to a method for preventing and/or treating disorders associated to the human herpesvirus 8 (HHV8), comprising the administration to a person in need thereof of an effective dose of the pharmaceutical composition as defined above.

The present invention also relates to the use of the pharmaceutical composition as defined above, for the manufacture of a drug for the prevention and/or the treatment of disorders associated to the human herpesvirus 8 (HHV8).

The disorders associated to the human herpesvirus 8 (HHV8) may be in particular human Kaposi sarcoma (KS), primary effusion lymphoma (PEL) and multicentric Castleman disease (MCD).

The disorders associated to the human herpes virus 4 (HHV4) may be:
  infectious mononucleosis (glandular fever);
  lymproliferative disorders such as Hodgkin's lymphoma, Burkitt's lymphoma, central nervous system lymphomas, plasmablastic lymphoma, diffuse large B cell lymphoma and primary effusion lymphoma;
  non lymphoid malignancies such as nasopharyngeal carcinoma and gastric cancer; and
  autoimmune diseases such as Dermatomyositis, systemic lupus erythematosus, rheumatoid arthritis, Sjögren's syndrome, multiple sclerosis.

The examples which follow illustrate the invention without limiting its scope in any way.

HHV8 infected cell line (BC3), HHV8-non infected cell lines (MRC5, HeLa P4), and HHV8 non infected primary cells (human keratinocytes, human cutaneous fibroblasts, B-type lymphocytes CD19+) were grown in vitro and treated by either Primaquine diphosphate, Hycanthone, Paclitaxel or Doxorubicin hydrochloride at a concentration of 10 µM. Cell viability was evaluated by ATP quantitation 48 h after the treatment started. Figure shows the relative cell viability (%) as expressed as the percentage of treated- vs untreated control-cells. Paclitaxel and Doxorubicine are shown to highlight the high specificity of Primaquine diphosphate and Hycanthone activity for HHV-8 infected cells.

Figure 2:
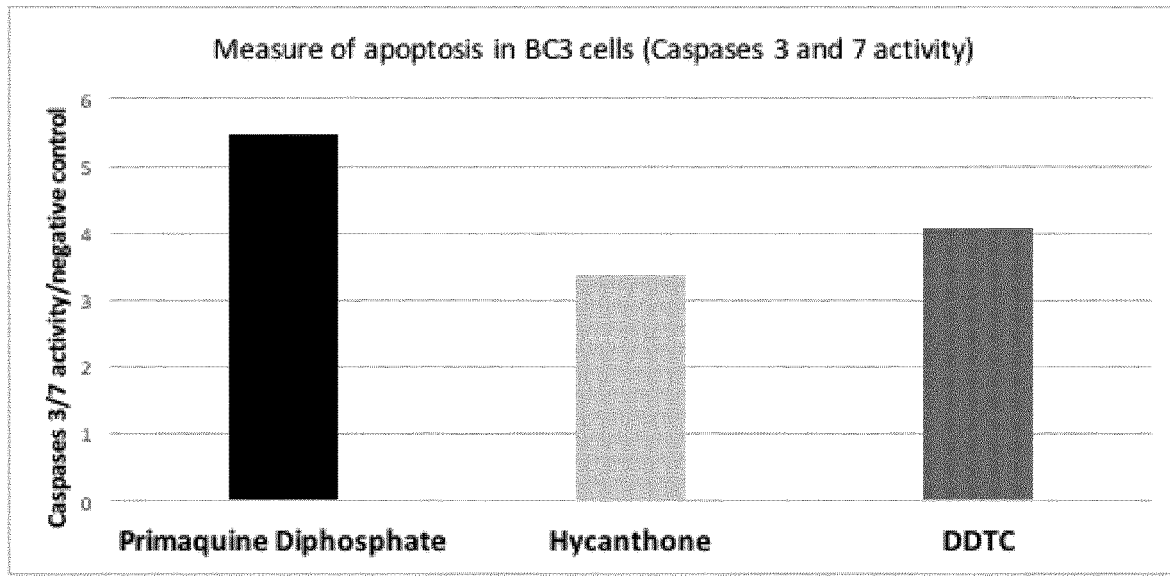

FIG. 2: Apoptosis induction in BC-3 cell lines exposed to Primaquine diphosphate, Hycanthone and Diethyldithiocarbamate.

BC-3 cells were grown in vitro and treated by either Primaquine diphosphate, Hycanthone, or Diethyldithiocarbamate (DDTC) at a concentration of 10 µM. Apoptosis induction was evaluated 24 h after the treatment started by measuring caspase 3/7 activity in treated- or untreated control BC-3 cells. Figure shows the fold increase of caspase 3/7 activity in treated- vs untreated control-cells. DDTC is used as a positive inducer of caspase 3/7 activity in BC-3 cell lines (Matsuno et al., 2012, Int J Oncol 40: 1071-1078).

Figure 3:
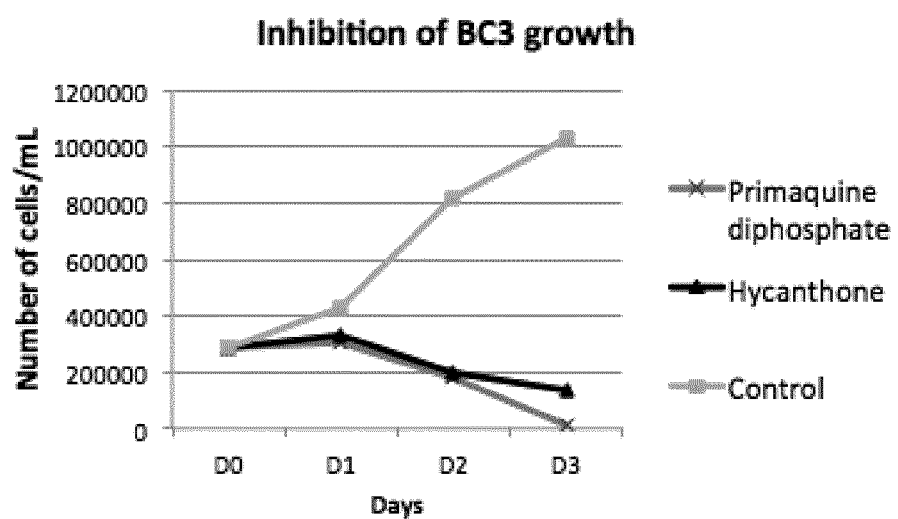

FIG. 3: Inhibition of BC-3 cell growth in presence of Primaquine diphosphate or Hycanthone.

BC-3 cells were grown in vitro and treated by either Primaquine diphosphate or Hycanthone at a concentration of 10 µM. Cell growth was measured every day from the day of treatment (DO) until 3 days after the treatment started (D3). Figure shows the BC-3 growth curve exposed to Primaquine diphosphate (black triangle) or Hycanthone (black square) in comparison to cells that were grown in standard condition (black circle).

Figure 4A:
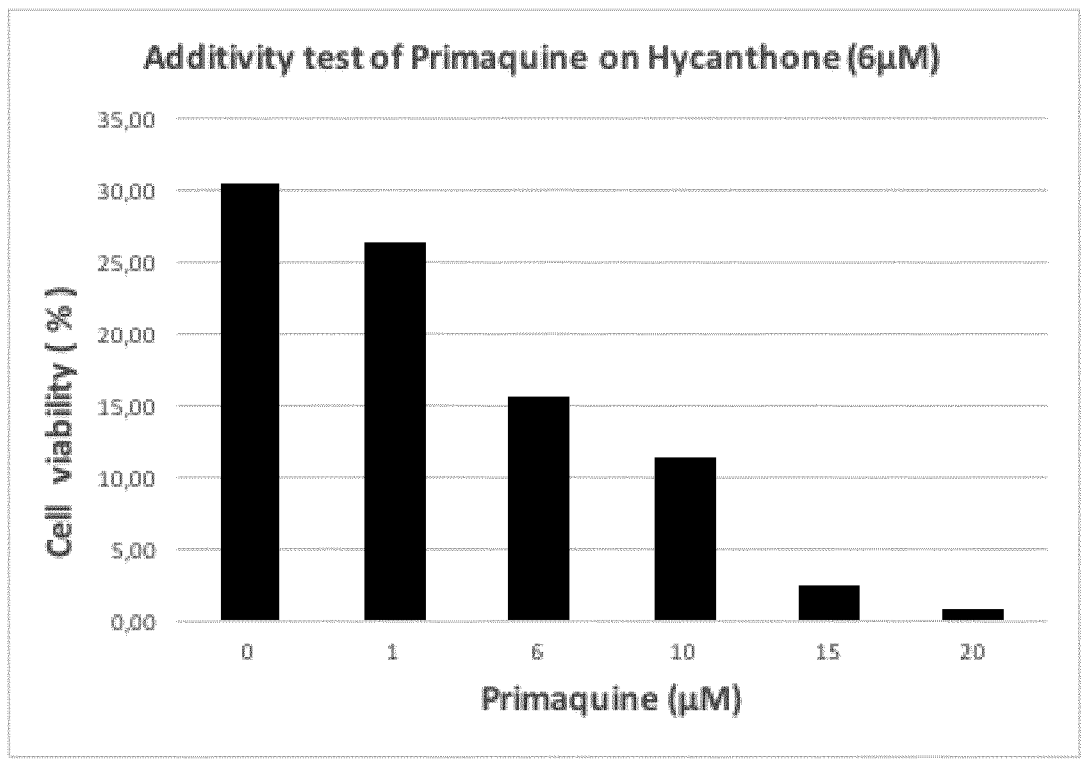

FIG. 4: Additive effect of Primaquine and Hycanthone on cell death. Percentage of cell viability in BC3 (production of ATP at 48 hours) in presence of (A) fixed concentration of Hycanthone (6 µM) with increased concentration of Primaquine (0 to 20 µM) or (B) fixed concentration of Primaquine (6 µM) with increased concentration of Hycanthone (0 to 20 µM).

Figure 5A:
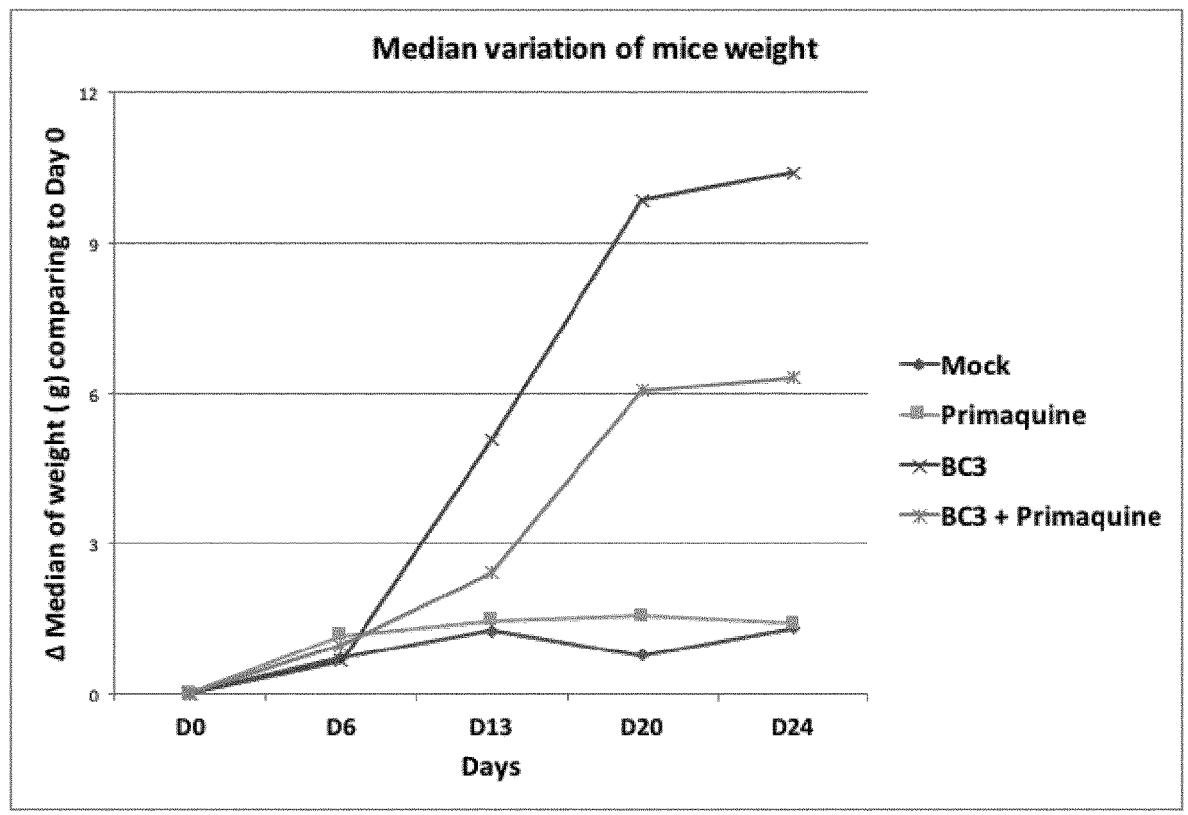
Figure 5B:
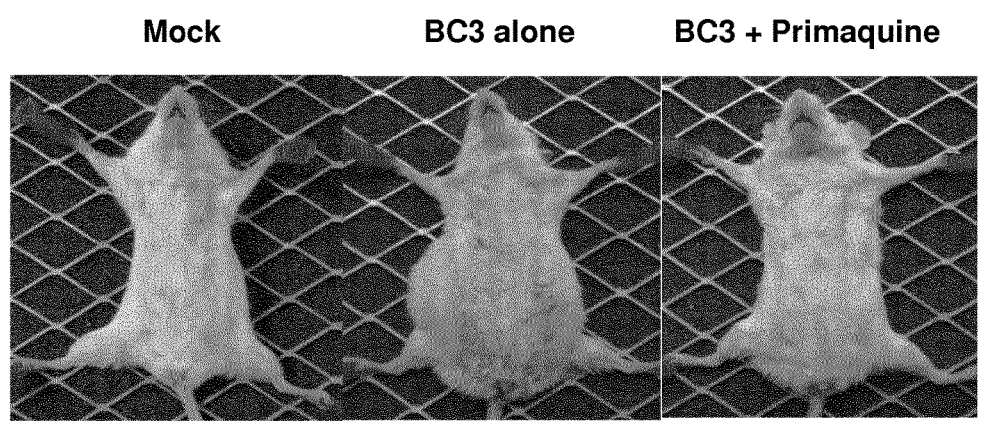

FIG. 5: In vivo evaluation of Primaquine efficacy in a Primary Effusion Lymphoma xenograft model in immunodeficient NOD/SCID mice.

Primaquine efficacy was evaluated using a mice model of immunodeficient NOD/SCID mice. Four experimental group were designed: Mice "Mock" (n=6) that did not received BC-3 graft nor primaquine treatment, mice "Primaquine" (n=6) that did not received BC-3 graft but received primaquine treatment (12, 5 mg/kg), mice BC-3 (n=6) that received BC-3 xenograft (BC-3 20.10$^6$ cells) but no primaquine treatment and mice "BC-3+primaquine (n=6) that received both BC-3 xenograft (BC-3 20.10$^6$ cells) and primaquine treatment (12, 5 mg/kg). Mice weight was measured at various times (D6, D13, D20 and D24) after the treatment started. Figure A shows the median variation of the mice weight between baseline and D24. Primaquine (given 12.5 mg/kg 3 times a week) reduces of 39.4% the median gain of weight at D24 comparing to untreated mice (BC3).

Figure B shows picture of mice of the "Mock", "BC-3" and "BC-3+primaquine" experimental groups after 24 days of treatment. Note the large growth tumor in the abdomen of the mouse that received BC-3 xenograft ("BC-3") but not treated by primaquine. In contrast, the mouse that received both BC-3 xenograft and primaquine treatment ("BC-3+primaquine") showed a reduced growth tumor in the abdomen.

FIG. 6: Primaquine and hycanthone inhibit IκB phosphorylation in PEL cell line.

BC-3 cells were pre-treated for 6 h (A) and 12 h (B) with primaquine and hycanthone at 10 µM. DDTC was used as positive control. Whole-cell lysates were prepared as described in Materials and Methods of example F and used for p-IκB western blot analysis by using the appropriate antibodies. The blot was stripped and reprobed with an antibody directed against IκB to demonstrated no change in the total IκB amount in the cell; and with an antibody against β-actin to demonstrate equal loading of proteins in different lanes. Treatment of BC-3 cells with DDTC (diethyldithiocarbamate) was carried out in the same conditions and served as a positive control.

EXAMPLES

Materials and Methods

Biological Activities of the Compounds According to the Invention

A—Cell Viability

Materials and Methods

The effect of Primaquine diphosphate (Sigma), Hycanthone (Sigma), Paclitaxel (Sigma), and Doxorubicin (Sigma) were evaluated on relevant primary cells and cell lines that are or not infected by HHV-8.

Cells evaluated were:
  BC-3: cell line established from pleural effusion from a human immunodeficiency virus (HIV) negative patient diagnosed with primary effusion lymphoma (PEL). BC-3 cell line is HHV8 infected but not infected for Epstein-Barr virus (EBV) as well as for herpes simplex virus 1 &2 (HSV-1 & HSV-2) and cytomegalovirus (CMV) (ATCC),
  MRC5: Cell line derived from normal lung tissue of a 14-week old male fetus (ATCC),
  Primary cutaneous fibroblasts (Lonza ref CC 25 11),
  Primary keratinocytes (Lonza ref 00 192 627),
  HeLa: immortal cell line established from an adult human cervical cancer HVP-18 infected (NIH Reagent program),
  Primary B-type lymphocytes CD19+: primary B cells positively selected using CD19 microbeads (Miltenyi).

Cells were treated in vitro with either Primaquine diphosphate (Sigma), Hycanthone (Sigma), Paclitaxel (Sigma), or Doxorubicin hydrochloride (Sigma) at a concentration of 10 µM. The viability of the cells was evaluated 48 h after the treatment started as previously described with the Kit Cell-Titer Glo (Promega).

Results

Figure 1:
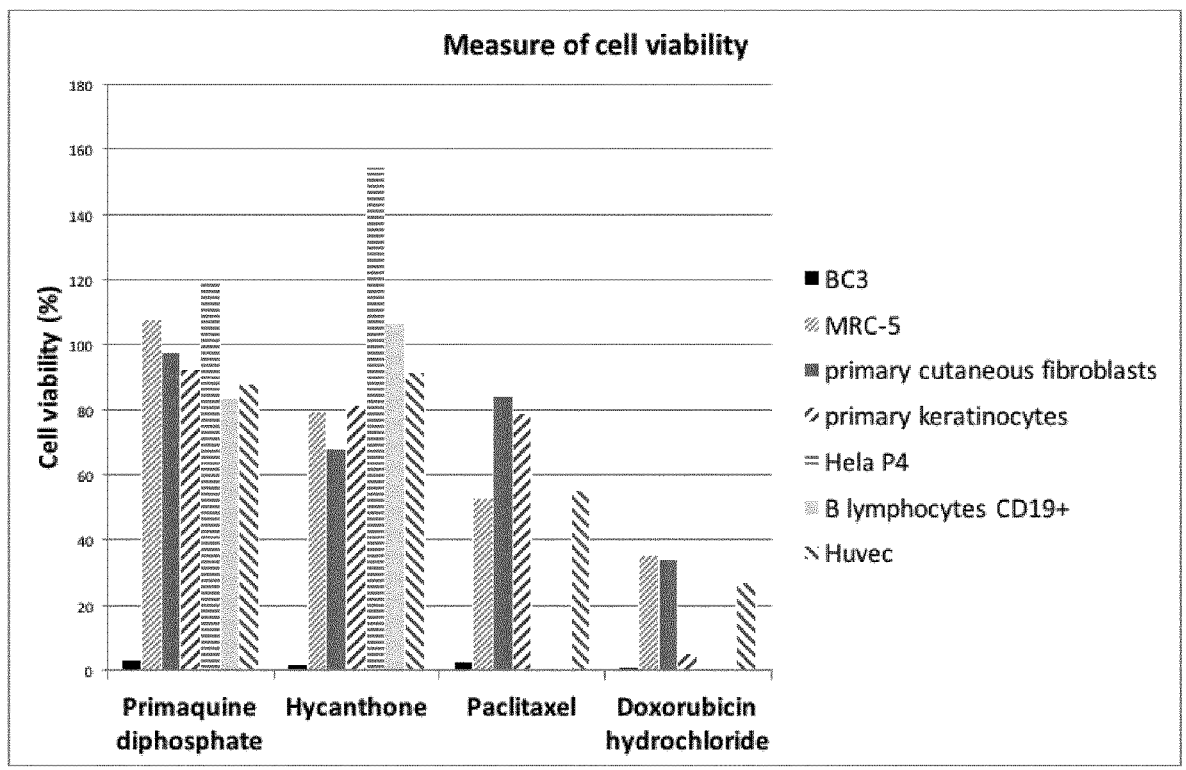
FIG. 1: Viability of HHV8-infected and non-infected human cells in presence of Primaquine diphosphate, Hycanthone, Paclitaxel, or Doxorubicin.

Primaquine diphosphate and hycanthone induced more than 90% of cell death in BC-3 cells that are HHV8 infected, without toxicity (<20% of cell death) in other cells types non infected by HHV8 (MRC-5, primary cutaneous fibroblasts, primary keratinocytes, Hela P4) (FIG. 1). Paclitaxel and doxorubicin were used as controls. Paclitaxel and doxorubicin induced cell death in BC-3 but are also toxic (>20% of cell death) in other cells types non-infected by HHV8 (FIG. 1).

B—Induction of Caspase Activity

Materials and Methods

BC-3 cells (10000 cells/well) were incubated 24 h with a concentration of 10 µM of Primaquine diphosphate (Sigma), Hycanthone (Sigma), or Diethyldithiocarbamate (DDTC) (Sigma), and then lysed and a 3/7 Reagent (DEVD) is added. Lysed cells release caspase-3 or -7, which cleave the DEVD substrate from the aminoluciferin. Finally, the oxidation of the luciferin by luciferase produces light, which is measured by a luminometer. The amount of light produced is proportional to the amount of caspase-3 or -7 activity. Disulfiram (DDTC) (Sigma) known to induce apoptosis in BC-3 cells via the inhibition of NF-κB is used as positive control.

Results

Primaquine and Hycanthone induced cell death in BC-3 by apoptosis (caspases 3/7 activation) (FIG. 2). Apoptosis induced by Primaquine and Hycanthone was at least as equivalent of that induced by DDTC (DDTC was used as positive control and was able to induce cell death by apoptosis 4 times superior than non-treated control) (FIG. 2).

C—Cell Growth Inhibition

Materials and Methods

BC-3 cells were grown in RPMI-1640 GlutaMAX (Gibco) supplemented with 10% fetal bovine serum and antibiotics (amikacine and vancomycine) during 3 days. The number of cells per milliliter is measured at baseline, DO, D2 and D3. BC-3 were cultured with and without primaquine and Hycanthone.

Results

Primaquine diphosphate and Hycanthone inhibited cellular growth of BC3 in comparison with BC3 cells cultured in standard conditions (FIG. 3).

D—Additivity of Primaquine and Hycanthone

Materials and Methods

Figure 4B:
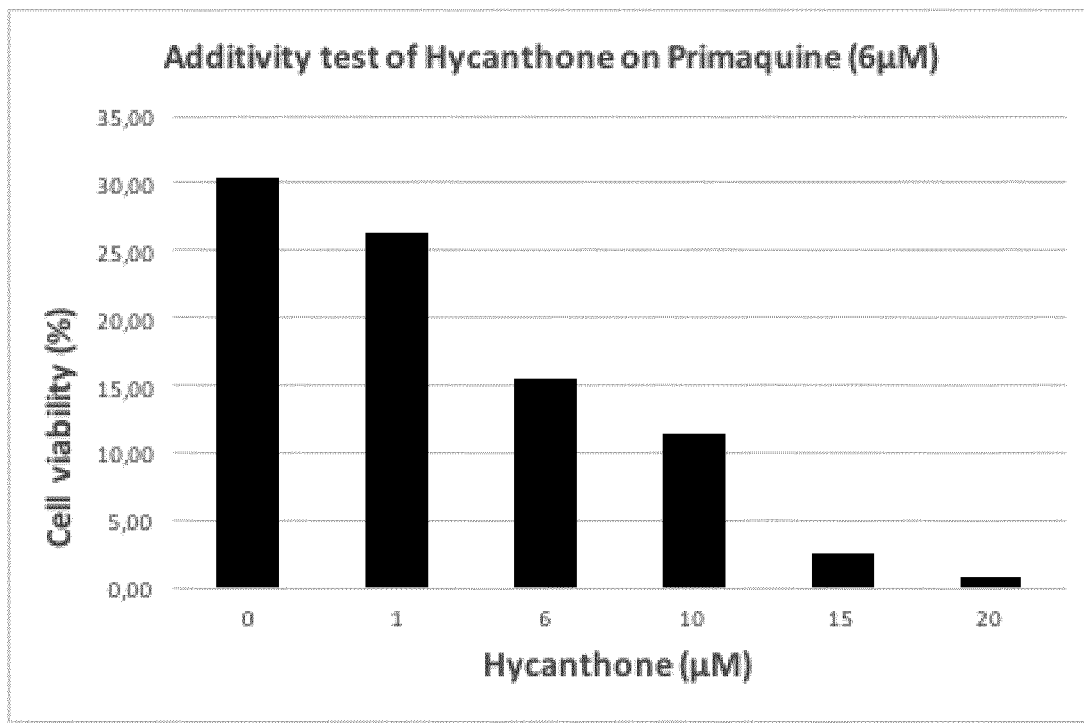

BC-3 cells were treated in vitro either with Hycanthone at a concentration of 6 µM and with different concentrations of Primaquine diphosphate (0, 1, 6, 10 15 and 20 µM) (FIG. 4A) or with Primaquine diphosphate at a concentration of 6 µM and with different concentrations of Hycanthone (0, 1, 6, 10 15 and 20 µM) (FIG. 4B). The viability of the cells was evaluated 48 h after the treatment started as previously described with the Kit cell Titer Glo.

Results

Primaquine diphosphate and Hycanthone have an additive effect on inducing BC3 cell death (FIGS. 4 A & B).

E—Evaluation of Primaquine Efficacy in a Primary Effusion Lymphoma Xenograft Model in Immunodeficient NOD/SCID Mice.

In order to confirm the anti-tumoral effect of the molecules identified in vitro, a model of PEL in immunodeficient NOD/SCID mice has been used.

Materials and Methods

At baseline, mice are inoculated with a PEL cell line (BC-3) by intraperitoneal (i.p) injection. One day after injection of BC-3 cells, Primaquine is administered by intraperitoneal injection, and then 3 times a week during 8 weeks. Tumoral burden is evaluated by the measure of weight every weeks (References: T. Matsuno, 2012: Diethyldithiocarbamate induces apoptosis in HHV-8-infected primary effusion lymphoma cells via inhibition of the NF-κB pathway; K. A. Sarosiek, 2010: Efficacy of bortezomib in a direct xenograft model of primary effusion lymphoma; W. Wu, 2005: Inhibition of HHV-8/KSHV infected primary effusion lymphomas in NOD/SCID mice by azidothymidine and interferon).

The experiment was conducted on 24 NOD/SCID mice (4 groups of 6 mice) (Charles River laboratories): 1 group (Mock) without xenograft (no BC-3) and non-treated (no Primaquine), 1 group with xenograft (BC-3) and non-treated (no Primaquine), 1 group with xenograft (BC-3) and treated (Primaquine 12.5 mg/kg; (Sigma), 1 group without xenograft and treated (Primaquine 12.5 mg/kg; (Sigma).

At the beginning of the experiments, the mice were 6 weeks old according to previous experiments conducted and available in the literature. Animals had 7 to 10 days of acclimatization before experiment. At baseline, $20.10^6$ of BC3 cells in 500 µL of PBS were injected by i.p. in order to induce the development of PEL. Tumor growth is correlated with the total gain of weight. The consequent gain of weight should not exceed 150% of the baseline weight. For the group of mice with xenograft (BC-3) and non treated by Primaquine, each mice received 1 i.p injection of 500 µL of PBS instead of BC-3 cells in order to evaluate the toxicity of Primaquine in mice.

Results

Primaquine reduced (39.4%) the gain of weight in mice with xenograft and treated versus mice with xenograft and non treated (FIGS. 5A & B). Primaquine did not show any toxicity in mice after 24 days of treatment.

F—Complementary Data for Signaling Pathways Analysis

In order to investigate the molecular mechanism involved in the HHV-8-infected cell death when they were treated with primaquine and hycanthone, we analyzed the NF-κB pathway which was shown to be constitutively active in PEL cell lines, associated with persistent phosphorylation of IκB (Liu et al., 2002).

Materials and Methods

Cell Culture and Protein Extraction:

BC-3, an HHV-8 positive lymphoblastic cell line (ATCC CRL-2277) and RAMOS, an human Burkitt's lymphoma cell line (ATCC CRL-1596), were routinely maintained in RPMI 1640 medium supplemented with 10% fetal heat-inactivated bovine serum (FBS), and antibiotics (Sigma Chemical Co., St. Louis, Mo.) in a 5% $CO_2$ incubator at 37° C. To prepare whole cell extracts, the cells were washed with cold phosphate-buffered saline twice and lysed in lysis RIPA buffer containing 10 mM Tris-HCl, pH 8.0, 140 mM NaCl, 1% Triton X-100, 1 mM EDTA, 0.5 mM EGTA, 0.1% sodium deoxycholate, 0.1% SDS, supplemented with protease inhibitor mixture (1 mM PMSF, 10 mM β-glycerophosphate, 10 mM NaF, 1 mM sodium orthovanadate, 1 mM sodium pyrophosphate), (ThermoFisher Scientific) at 4° C. for 30 min. After incubation, the mixture was pipetted five or six times to disperse the cells followed by centrifugation at 14,000 rpm at 4° C. for 10 min. The supernatants were collected as whole cell extracts, and protein concentration was determined by the Lowry method.

Western Blot Analysis:

200 µg of whole cell extracts were separated by electrophoresis (LDS-PAGE) under denaturing conditions with NuPAGE Novex 4-12% Bis-Tris gel (1 mm, 12 wells, Invitrogen, UK) and proteins were transferred onto nitrocellulose membranes and saturated in 20 ml of saturation buffer consisting of TBS 1× (Tris Buffered Saline) containing 200 mM Tris, 1.4 M NaCl (pH 7.6), 5% no fat milk, 0.1% Tween 20 for 1 h. After washing three times for 15 min with 15 ml of TBS/T buffer [1×TBS, 0.1% Tween-20], membranes were incubated overnight with gentle mixing at 4° C. with 10 ml of rabbit polyclonal primary antibodies against human IκB (SC-371, 1:2000), p-IκB (SC-7977, 1:200), and mouse monoclonal antibody against human β-actin, used to control loading, (SC-47778, 1:1000) diluted in TBS/T supplemented with 5% BSA (all antibodies were purchased from Santa Cruz Biotechnology, Inc., Santa Cruz, Calif., USA). After washing to remove unbound antibodies, bound primary antibodies were detected by incubation for 1 h using secondary antibody against rabbit- and mouse-IgG (Santa Cruz Biotechnology, SC-2357, 1:5000 and SC-2005, 1:5000, respectively). Unbound material was removed by washing and peroxidase activity was detected in a chemiluminescence assay (WesternBright ECL, Advansta, Menlo Park, USA).

Results

Figures 6A, 6B:
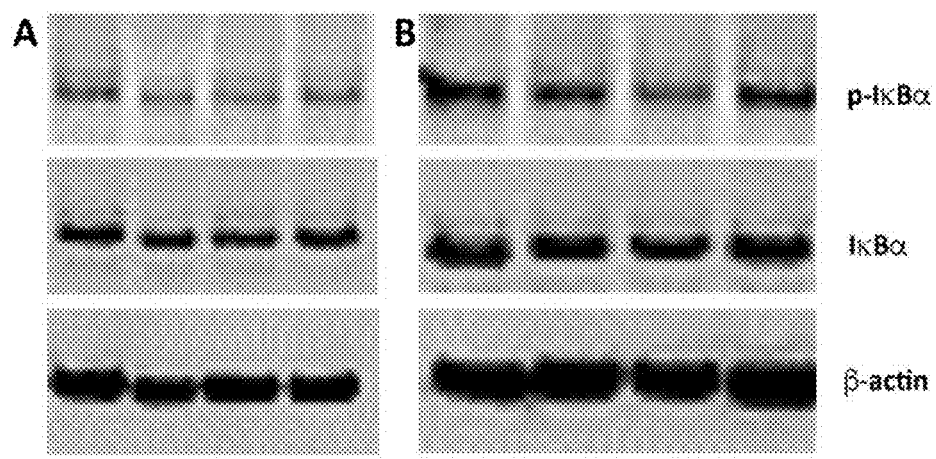

Using the BC-3 PEL cell line, we confirmed the constitutive activation of the IκB pathway (FIG. 6) and shown that when cells were pre-treated with primaquine and hycanthone for 6 and 12 h, the phosphorylation of IκB was dramatically reduced (FIGS. 6A and 6B). Positive control (DDTC) used in parallel and shown a decrease on the phosphorylation of IκB as well. Our data demonstrated that the activation of HHV-8 positive cell cell death by primaquine and hycanthone would be linked to the inhibition of the NF-κB activation.

The invention claimed is:

1. A method for preventing and/or treating disorders associated with the human herpesvirus 8 (HHV8) or the human herpes virus 4 (HHV4), comprising administering to a subject in need thereof, an effective amount of a compound of following general formula (I):

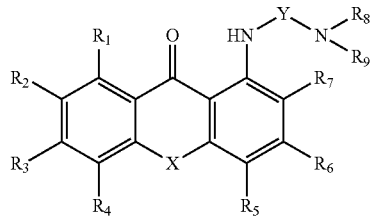

(I)

or a pharmaceutically acceptable salt and/or solvate thereof, wherein:

X is an oxygen or a sulfur atom;
Y is a $(C_1-C_{10})$alkyl group;
$R_1$ to $R_4$ are, independently of one another, hydrogen atom, halo, —$CF_3$, —CN, —$CO_2R_{10}$, —$CONR_{12}R_{13}$, —$NO_2$, or a group selected from $(C_1-C_6)$alkyl, $(C_2-C_6)$alkenyl and $(C_2-C_6)$alkynyl;
$R_5$ to $R_7$ are, independently of one another, hydrogen atom or a group selected from $(C_1-C_6)$alkyl, —$OR_{14}$, —$NR_{15}R_{16}$, —$CONR_{17}R_{18}$, —$CO(NR_{19}R_{20})$, —$SR_{21}$, —$COR_{22}$, —$COOR_{23}$, —$SO_2R_{24}$, —$NO_2$ and —$NO^+$, said $(C_1-C_6)$alkyl group being optionally substituted with one or several groups selected from halo, —$OR_{25}$, —$NR_{26}R_{27}$, —$CONR_{28}R_{29}$, —$CO(NR_{30}R_{31})$, —$SR_{32}$, —$COR_{33}$, —$COOR_{34}$, —$SO_2R_{35}$, —$NO_2$ and —$NO^+$;
$R_8$ and $R_9$ are, independently of one another, hydrogen atom or a $(C_1-C_{10})$alkyl group optionally substituted with OH, or $R_8$ and $R_9$ form together with the nitrogen atom to which they are chemically linked, an heterocycle;
$R_{10}$ to $R_{35}$ are, independently of one another, hydrogen atom, halo or a $(C_1-C_6)$alkyl group.

2. The method of claim 1, wherein X is a sulfur atom.

3. The method of claim 1, wherein Y is a $(C_1-C_6)$alkyl group.

4. The method of claim 1, wherein said compound is a compound of the following general formula (Ia):

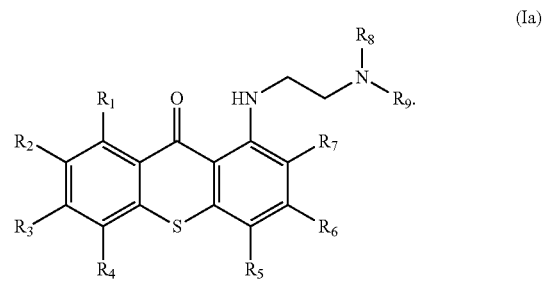

(Ia)

5. The method of claim 1, wherein $R_8$ and $R_9$ are, independently of one another, a $(C_1-C_{10})$alkyl group.

6. The method of claim 1, wherein $R_1$ to $R_4$ are, independently of one another, hydrogen atom, halo, or a group selected from $(C_1-C_6)$alkyl and $(C_2-C_6)$alkenyl.

7. The method of claim 1, wherein $R_5$ to $R_7$ are, independently of one another, hydrogen atom or a $(C_1-C_6)$alkyl group optionally substituted with one or several groups selected from, halo, —$OR_{25}$, —$NR_{26}R_{27}$, —$CONR_{28}R_{29}$, —$CO(NR_{30}R_{31})$, —$SR_{32}$, —$COR_{33}$, —$COOR_{34}$, —$SO_2R_{35}$, —$NO_2$ and —$NO^+$; $R_{25}$ to $R_{35}$ being as defined in claim 1.

8. The method of claim 1, wherein $R_6$ and $R_7$ are hydrogen atom and $R_5$ is a $(C_1-C_6)$alkyl group substituted with OH.

9. The method of claim 1, wherein said compound is a compound of the following formula (Ib):

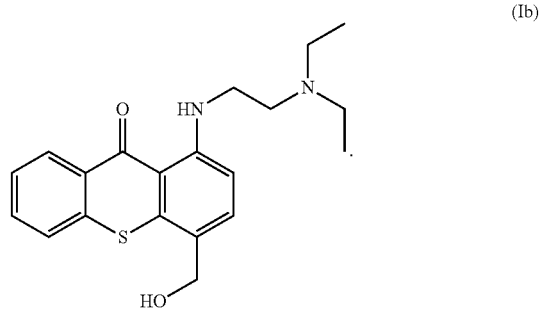

(Ib)

10. A method for preventing and/or treating disorders associated with the human herpesvirus 8 (HHV8), comprising administering to a subject in need thereof, an effective amount of compound of following general formula (II):

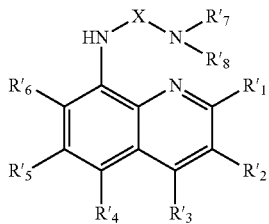

(II)

or a pharmaceutically acceptable salt and/or solvate thereof, wherein:

X is a $(C_1-C_{10})$alkyl group;

$R'_1$ to $R'_3$ are, independently of one another, hydrogen atom, halo, $-OR'_9$, $-R'_{10}R'_{11}$, $-SR'_{12}$, $-COSR'_{13}$, $-NR'_{14}R'_{15}$, $-COR'_{16}$, $-COOR'_{17}$ or a $(C_1-C_6)$alkyl group;

$R'_4$ to $R'_6$ are, independently of one another, hydrogen atom, halo, $-OR'_{18}$, $-R'_{19}OR'_{20}$, $-SR'_{21}$ or $-NR'_{22}R'_{23}$;

$R'_7$ and $R'_8$ are, independently of one another, hydrogen atom or a $(C_1-C_{10})$alkyl group, or $R'_7$ and $R'_8$ form together with the nitrogen atom to which they are chemically linked, an heterocycle;

$R'_9$ to $R'_{23}$ are, independently of one another, hydrogen atom, halo or a group selected from $(C_1-C_6)$alkyl, aryl, $(C_1-C_6)$alkylaryl group.

11. The method of claim 10, wherein X is a $(C_1-C_6)$alkyl group.

12. The method of claim 10, wherein said compound is a compound of the following general formula (IIa):

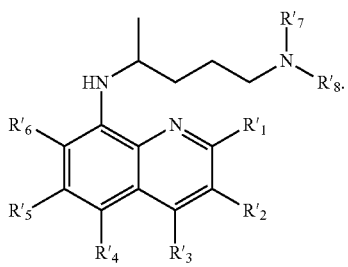

(IIa)

13. The method of claim 10, wherein $R'_7$ and $R'_8$ are, independently of one another, an hydrogen atom or a $(C_1-C_{10})$alkyl group.

14. The method of claim 10, wherein $R'_1$ to $R'_3$ are, independently of one another, hydrogen atom, $-OR'_9$, $-SR'_{12}$, $-COSR'_{13}$, $-NR'_{14}R'_{15}$ or a $(C_1-C_6)$alkyl group; $R'_9$ to $R'_{15}$ being as defined in claim 10.

15. The method of claim 10, wherein $R'_4$ to $R'_6$ are, independently of one another, hydrogen atom, halo, $-OR'_{18}$ or $-R'_{19}OR'_{20}$, $R'_{18}$ to $R'_{20}$ being as defined in claim 10.

16. The method of claim 10, wherein said compound is a compound of the following formula (IIb):

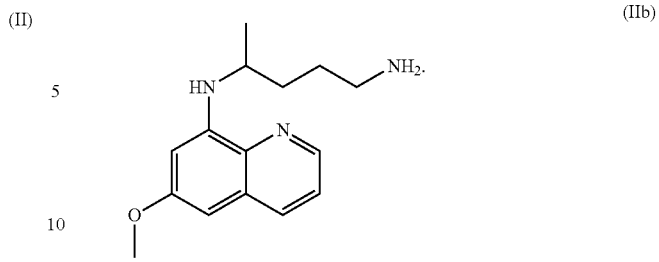

(IIb)

17. A method for preventing and/or treating disorders associated with the human herpesvirus 8 (HHV8) or the human herpes virus 4 (HHV4), comprising administering to a subject in need thereof, an effective amount of a pharmaceutical composition comprising at least one compound of claim 1 and at least one pharmaceutically acceptable excipient.

18. The method of claim 17, wherein said composition further comprises another active principle selected from the group consisting of Bleomycine, Vinblastine, paclitaxel and docetaxel, daunorubicine liposomiale, adriamycine, vincristine, navelbine, gemcitabine, interferon α, all-transretinoic acid, thalidomide, IL-12, IL-4, Panretin, Revlimid, lenalinomide, rituximab, etoposide, cyclophosphamide, doxorubicin, vincristin, prednisone, cidofovir, foscarnet, ganciclovir, valganciclovir, Tocilizumab, siltuximab, bortezomib, RNAi against LANA and/or vFlip, Hydroxyurea, and Rapamycin.

19. The method of claim 1,
wherein said disorders associated with the human herpesvirus 8 (HHV8) are selected from human Kaposi sarcoma (KS), primary effusion lymphoma (PEL) and multicentric Castleman disease (MCD);
and wherein said disorders associated with the human herpes virus 4 (HHV4) are selected from:
infectious mononucleosis (glandular fever);
lymproliferative disorders;
non lymphoid malignancies; and
autoimmune diseases.

20. The method of claim 10,
wherein said disorders associated with the human herpesvirus 8 (HHV8) are selected from human Kaposi sarcoma (KS), primary effusion lymphoma (PEL) and multicentric Castleman disease (MCD).

21. The method of claim 17,
wherein said disorders associated with the human herpesvirus 8 (HHV8) are selected from human Kaposi sarcoma (KS), primary effusion lymphoma (PEL) and multicentric Castleman disease (MCD);
and wherein said disorders associated with the human herpes virus 4 (HHV4) are selected from:
infectious mononucleosis (glandular fever);
lymproliferative disorders;
non lymphoid malignancies; and
autoimmune diseases.

22. A method for preventing and/or treating disorders associated with the human herpesvirus 8 (HHV8), comprising administering to a subject in need thereof an effective amount of a pharmaceutical composition comprising at least one compound of claim 10 and at least one pharmaceutically acceptable excipient.

23. The method of claim 22, wherein said composition further comprises another active principle selected from the group consisting of Bleomycine, Vinblastine, paclitaxel, docetaxel, daunorubicine liposomiale, adriamycine, vincristine, navelbine, gemcitabine, interferon α, all-transretinoic acid, thalidomide, IL-12, IL-4, Panretin, Revlimid, lenalinomide, rituximab, etoposide, cyclophosphamide, doxorubicin, vincristin, prednisone, cidofovir, foscarnet, ganciclovir, valganciclovir, Tocilizumab, siltuximab, bortezomib, RNAi against LANA and/or vFlip, Hydroxyurea, and Rapamycin.

24. The method of claim 22, wherein said disorders associated with the human herpesvirus 8 (HHV8) are selected from the group consisting of human Kaposi sarcoma (KS), primary effusion lymphoma (PEL), and multicentric Castleman disease (MCD).

* * * * *